United States Patent [19]

Top et al.

[11] Patent Number: 5,190,618
[45] Date of Patent: Mar. 2, 1993

[54] PRODUCTION OF HIGH CONCENTRATION TOCOPHEROLS AND TOCOTRIENOLS FROM PALM-OIL BY-PRODUCTS

[75] Inventors: Abdul G. Md. Top, Kuala Lumpur; Leong W. Leong, Shah Alam; Augustine S. H. Ong, Kuala Lumpur, all of Malaysia; Tsukasa Kawada, Tokyo, Japan; Hisashi Watanabe, Tokyo, Japan; Nozomu Tsuchiya, Tokyo, Japan

[73] Assignees: Bioindustry Development Centre (BIDEC), Tokyo, Japan; Palm Oil Research & Development Board, Selanger, Malaysia

[21] Appl. No.: 332,238

[22] Filed: Mar. 31, 1989

[51] Int. Cl.⁵ .................... B01D 1/24; B01D 3/12; B01D 3/34; C07D 311/72

[52] U.S. Cl. ........................................ 203/34; 159/49; 159/DIG. 16; 203/36; 203/38; 203/48; 203/49; 203/77; 203/80; 203/89; 203/DIG. 6; 210/672; 549/413

[58] Field of Search ............... 203/48, 73, 80, DIG. 6, 203/DIG. 16, 34, 38, 89, 49, 36, 77, 73, 74; 549/413; 210/672; 34/15; 422/26; 159/49, DIG. 16

[56] References Cited

U.S. PATENT DOCUMENTS

| | | | |
|---|---|---|---|
| 2,349,789 | 5/1944 | Hickman | 549/413 |
| 2,497,317 | 2/1950 | McFarlane | 549/413 |
| 2,704,764 | 3/1955 | Mattikau et al. | 549/413 |
| 3,122,565 | 2/1964 | Kijima et al. | 549/413 |
| 4,454,329 | 6/1984 | Takagi et al. | 549/413 |
| 4,550,183 | 10/1985 | Willging | 549/413 |
| 4,594,437 | 6/1986 | Sampath Kumar | 549/413 |
| 4,607,111 | 8/1986 | Foster | 549/413 |
| 4,882,441 | 11/1989 | Coffen et al. | 549/407 |

FOREIGN PATENT DOCUMENTS

| | | | |
|---|---|---|---|
| 0171009 | 2/1986 | European Pat. Off. | 549/413 |
| 0005179 | 1/1984 | Japan | 549/413 |
| 2090836 | 7/1982 | United Kingdom | 549/413 |
| 2117381 | 10/1983 | United Kingdom | 549/413 |

OTHER PUBLICATIONS

IUPAC-IUB-Commission on Biochemical Nomenclature (CBM), Nomenclature of Tocopherols and Related Compounds-Recommendation. Eur. J. Biochem. 46, 217-219 (1974).

Primary Examiner—Virginia Manoharan
Attorney, Agent, or Firm—Willian Brinks Olds Hofer Gilson & Lione

[57] ABSTRACT

A process for the production of tocopherols (T) and tocotrienols (T3) from palm fatty acid distillates (PFAD). The process includes converting free fatty acids and glycerides in PFAD into alkyl esters, then separating T and T3 from the alkyl esters and other impurities. The T and T3 are concentrated by ion-exchange and further concentrated by distilling the resulting product. Specific catalysts and optimum temperatures for the process are included. The resulting purified tocopherols and tocotrienols are useful substances, exhibiting antioxidant and physiological activities.

14 Claims, 1 Drawing Sheet

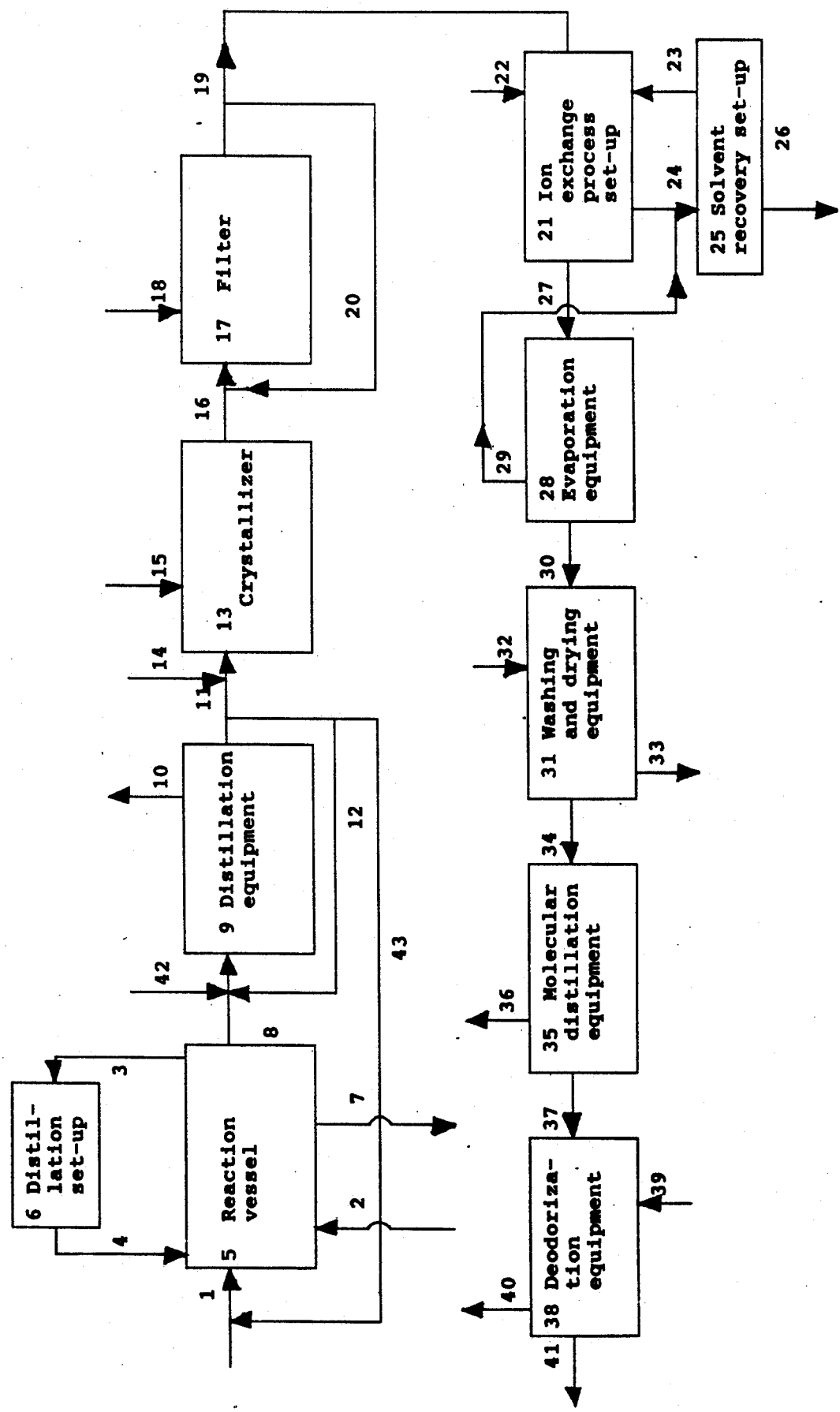

PRODUCTION OF HIGH CONCENTRATION TOCOPHEROLS AND TOCOTRIENOLS FROM PALM-OIL BY-PRODUCTS

BACKGROUND OF THE INVENTION

The present invention relates to a novel method for the production of tocopherols (T) and tocotrienols (T3) from palm oil by-products such as Palm Fatty Acid Distillate (PFAD).

Tocopherols and tocotrienols (tocopherol compounds having an unsaturated side chain) are very useful substances exhibiting strong antioxidant activities and physiological activities. PFAD is composed mainly of fatty acids, sterols, tocopherols, tocotrienols, squalene and like impurities. High concentrates of tocopherols and tocotrienols are not easily obtained by concentration of PFAD, however, because the amounts of tocopherols and tocotrienols in PFAD are very low compared to soyabean, rapeseed and similar raw materials.

Known processes for the concentration of tocopherols and tocotrienols usually use solvent extraction, solvent fractionation, ion-exchange resin treatment, etc., at the laboratory stage, but these processes are not complete or economically attractive. The present invention seeks to provide a combination of unit processes which produce better quality and better yield compared to the previous proposals. PFAD contains relatively high level of tocotrienols compared with other sources and this has not been commercially exploited. It is therefore an object of the present invention to provide a novel and efficient method for the production of tocopherols and tocotrienols from PFAD.

SUMMARY OF THE INVENTION

According to one aspect of the present invention, there is provided a process for the production of tocopherols (T) and tocotrienols (T3) from palm fatty acid distillates (PFAD) which comprises:

(1) converting free fatty acids and glycerides in PFAD into alkyl esters;

(2) separating T and T3 from the alkyl esters and other impurities;

(3) concentrating the T and T3 by ion-exchange; and (4) distilling the resulting product to produce a further concentrated T and T3 fraction.

More specifically, in accordance with the present invention, there is provided a process for production of tocopherols and tocotrienols from palm fatty acid distillates (PFAD) which comprises:

(a) treating the PFAD with an alkyl alcohol and appropriate catalysts to convert free fatty acids and glycerides into alkyl esters by esterification and transesterification, respectively;

(b) distilling the resulting product under reduced pressure to remove a major part of the alkyl esters and leave the tocopherols, tocotrienols (T and T3) and other higher boiling point substance in the residue;

(c) cooling the residue to bring about crystallization of higher-melting substances and other impurities and filtering off the crystalline material to leave the T and T3 in the filtrate;

(d) treating the filtrate from step (c) by an ion-exchange procedure with a high selectivity anionic resin to produce a concentrated T and T3 fraction;

(e) removing the solvent from the T and T3 fraction from step (d) by evaporation;

(f) washing and drying the product from step (e);

(g) subjecting the product from step (f) to molecular distillation to produce a further concentrated T and T3 product; and (h) deodorizing the T and T3 product.

In a modified form of the above process, the PFAD is pretreated (before esterification) by distillation to remove a major part of the free fatty acids.

By optimizing the conditions for the various steps described above, it is possible to produce a product having a high concentration of tocopherols and tocotrienols with very low losses of material during the process.

A discussion of the preferred conditions for the steps described above follows:

(a) It is preferred to use p-toluenesulfonic acid, hydrochloric acid or sulphuric acid as the catalyst for conversion of free fatty acid in PFAD into alkyl esters, at temperatures between 65° and 110° C. and reaction times of less than 3 hours.

Potassium hydroxide, sodium hydroxide or sodium methoxide are preferred as catalysts for conversion of glycerides into alkyl esters at temperature between 30° and 70° C., with reaction times of 10 minutes or more.

It is also preferred to treat the reaction mixture with a chelating agent such as ascorbic acid (Vitamin C), phosphoric acid, maleic acid, citric acid or tartaric acid, before drying and distillation.

(b) Distillation is preferably carried out using a high heat-transfer rate falling film vacuum distillation column, operating at below 10 torr (1333 N/m$^2$) and at a temperature between 100° and 200° C. Under such conditions, it is possible to concentrate T and T3 from 0.5% to more than 10%, with losses of T and T3 in the distilled alkyl esters being less than 1% based on the original raw material.

(c) It is preferred to concentrate T and T3 by using an anion-exchange resin column using methanol, ethanol or hexane as the eluting solvent and an acidic solution, such as sulphuric acid or boric acid, for desorbing T and T3 from the ion-exchange resin. Concentration from an initial 8% up to 80% or more can be achieved in this manner.

(e) Solvent evaporation is preferably carried out using a falling film evaporator and a rotary short path evaporator in series operating at 50° C. and 130° C. respectively, and under reduced pressure which minimizes denaturation of tocopherol and tocotrienols.

(g) It is preferred to carry out the molecular distillation at 140° to 220° C. under a vacuum below 0.05 torr (6.7 N/m$^2$). A T and T3 fraction with greater than 95% concentration can then be produced from raw materials containing a 60% concentration of T and T3.

The optional pretreatment (distillation) step is preferably carried out using a high heat-transfer rate falling film distillation column at temperatures between 150° and 250° C. and a vacuum below 10 torr (1333 N/m$^2$).

It is also preferred to minimize contact of tocopherols and tocotrienols with oxygen by nitrogen and/or nitrogen sparging throughout the various unit processes.

BRIEF DESCRIPTION OF THE DRAWING

The single FIG. of drawing is a block flow diagram illustrating the process of the invention.

DETAILED DISCLOSURE

As shown in the drawing, melted PFAD is fed into reaction vessel 5 via pipe system 1. A mixture of an alkyl alcohol and an acidic catalyst, such a p-toluenesulfonic acid (PTS), hydrochloric acid (HCl) or sulfuric acid, is introduced via pipe system 2. The reactants are heated and the esterification reaction is conducted at temperature between 65 and 110° C. Alkyl alcohol is continuously introduced into reaction vessel 5 via pipe system 4 and the evaporated alkyl alcohol is recovered and purified by the condensation and distillation set-up 6 via pipe system 3. When the reaction is completed, the reaction mixture is cooled. Another mixture of an alkyl alcohol and a catalyst, such as potassium hydroxide, sodium hydroxide or sodium methoxide, is added into reaction vessel 5 via pipe system 2. Transesterification of the glycerides proceeds at temperature between 30° and 70° C. and in reaction times of 10 minutes or more. After treatment with a chelating chemical (such as ascorbic acid (vitamin C), phosphoric acid, maleic acid, citric acid or tartaric acid), water washing, nitrogen sparging and drying, the resulting product is passed to distillation equipment 9 via pipe system 8. Effluent is discharged via pipe system 7.

Distillation equipment 9 consists of a high heat-transfer distillation column and distillate collection system. The distillation process is continuous. Alkyl esters are distilled at high vacuum at below 10 mm of Hg and at temperature between 100 and 200° C. Distilled alkyl esters are collected by condensation and discharged via pipe system 10 as a by-product. The retention time of T and T3 in the distillation column is short, so that deterioration is minimal. More than one distillation cycle may be practiced. Recycling of the heavy phase is by pipe system 12. The final heavy phase of distillation equipment 9 is a mixture of T, T3 and other substances found in PFAD and is passed to crystallizer 13 via pipe system 11.

The mixture in crystallizer 13 is heated until it is homogeneous and then cooled to 0–15° C. in 5–30 hours of cooling time, for example by a programmable automatic control system. Various quantities of solvent, such as acetone, ethanol and methanol, may or may not be added into the mixture in crystallizer 13 before cooling started, via pipe system 14. 0.5% or more of filter aid are added into crystallizer 13 via pipe system 15.

The mixture in crystallizer 13 is then passed to filter 17 where the crystallized substances are retained in filter cakes via pipe system 16. Before filtration is started, recycling of filtrate via pipe system 20 may be practiced in order to form sufficient cake thickness on the filter elements. Positive pressure filtration is practiced either by using a pump or by applying nitrogen gas via pipe system 18. The final filtrate, which is basically free of higher-melting substances, is passed to ion-exchange process set-up 21 via pipe system 19.

The filtrate is introduced into an ion-exchange column which consists of regenerated anion resin packing with high selectivity in adsorbing T and T3. An acidic solution such as sulfuric acid or boric acid is used to desorb T and T3 from the anion resin via pipe system 22. Solvent, such as methanol, ethanol or hexane, is used for elution of the various fractions in the ion-exchange process coming from solvent recovery set-up 25 via pipe system 23. Undesirable eluted fractions or effluent are discharged for solvent recovery or for other processing via pipe system 24 and 26, respectively, while the desired fractions which contain reasonably high concentrations of T and T3 are passed to evaporation equipment 28 via pipe system 27.

The evaporation system 28 is designed to provide short retention time for the T and T3 concentrate under vacuum that deterioration of T and T3 is minimal. Evaporated solvent is condensed and sent for purification via pipe system 29. The solvent-free T and T3 concentrate is passed to washing and drying equipment 31 via pipe system 30.

Water is added into a mixing vessel containing the T and T3 concentrate from evaporation equipment 28 via pipe system 32. Mixing and washing are conducted at elevated temperature under a nitrogen blanket. Effluent is discharged via pipe system 33. Drying is carried out in the same or different equipment by vacuum at temperature between 90–100° C. The resulting washed and dried product is passed to molecular distillation equipment 35 via pipe system 34.

Molecular distillation is carried out at very high vacuum. High concentration of the T and T3 fraction is obtained at temperatures between 140–220° C. and at vacuums below 0.05 torr (6.67 $N/m^2$). Undesirable fractions are discharged in pipe systems 36 while the high concentration T and T3 fraction is passed to deodorization equipment 38 via pipe system 37.

Deodorization is conducted at temperatures between 180 and 250° C. and at vacuums of 3–15 torr (400–2000 $N/m$). Low pressure steam is introduced into the deodorizer via pipe system 39 at a rate of 1–6% of the treated material. Distillate is collected by condenser via pipe system 40. Odorless, final, high-concentration T and T3 is sent for consumption via pipe system 41.

All the process equipment described above are equipped with nitrogen gas blanketing and nitrogen vacuum break systems for protecting T and T3 from oxidation.

Process 2

This process is similar to that of Process 1 except that the raw material, PFAD, is pretreated by removing majority of the free fatty acid in the PFAD by distillation before sending for processing by Process 1 at the same sequencing as described from (a) to (h) at Process 1.

As illustrated by the same FIG. as Process 1, PFAD is passed to the storage facility of distillation equipment 9 via pipe system 42. The distillation process is continuous. The majority of the free fatty acids are distilled at high vacuum, below 10 torr (1335 $N/m^2$) and at temperatures between 150 and 250° C. Distilled fatty acids are collected by condensation and discharged via pipe system 10. More than one distillation cycle may be practiced. Recycling is via pipe system 12. The final heavy phase is passed to reaction vessel 5 via pipe system 43. The processing conditions and products flow from reaction vessel 5 onward are same as the described in Process 1.

EXAMPLES

Process 1

Several experiments on Process 1 were conducted. The conditions of every step of Example 1 and Example 2 are shown in Tables 1.2–1.9, and the results are shown in Table 2.

During methyl esterification, methyl alcohol (MeOH) was fed continuously into the reaction vessel, and water which was by-produced during methyl esterification was removed continuously for effective reaction. The acid value decreased below 0.1 after methyl esterification. Almost all glycerides which are contained in the sample (about 10%) were transesterificated with catalyst. Ascorbic acid solution was used for protection of the T and T3 from denaturation. Samples were dried until the moisture was less than 0.5%.

Fatty acid methyl esters were removed by distillation. This treatment could achieve more than a 16-fold increase in concentration in view of the T and T3 concentration in the heavy phase, as shown in Table 2.

Impurities which have higher melting points than T and T3 in the heavy phase were removed by crystallization and filtration. Crystals appeared when the samples were cooled down, with or without several kinds of solvent. Crystals were removed by filtration by using the pressure of nitrogen gas.

The filtrates were loaded to regenerated anion-exchange resin in a column. Then the column was washed with 95% ethyl alcohol (EtOH) to purge impurities which did not attach to the ion-exchange resin. A 10% acid solution was used to desorb T and T3 from the resin, and then detached T and T3 were collected as a T and T3 fraction by using 96% EtOH.

Evaporations were conducted in 2 steps under the conditions described in Table 1.6. During the first step, mainly EtOH was evaporated. In the second step, solvents including water were evaporated completely. After evaporation of EtOH and water, the concentrations of T and T3 were 83.2% and 87.6%, respectively, as shown in Table 2.

Several batches of T and T3 were mixed. Water-soluble impurities could be removed from the sample by washing twice with water, followed by drying under the vacuum.

Further purification of T and T3 could be achieved by molecular distillations which were conducted in 2 steps. Firstly, at lower temperatures, impurities which are easy to be evaporated could be removed. Secondly, at higher temperatures, T and T3 could be evaporated. The impurities which show higher boiling points than T and T3 remained in the heavy phase.

Steam deodorization after molecular distillation produced the final product, which had no smell and was light brown in color.

Through our process as described above, little or no denaturation of T and T3 could be observed.

Process 2

Several experiments on Process 2 were conducted. The conditions of every step of Example 3 and Example 4 are shown in Tables 1.1–1.9. The results are shown in Table 2. Compared to the above process 1, the initial stage is different. First free acids in PFAD were distilled roughly before methyl esterification in order to decrease the quantity of material which is to be methyl esterificated. The succession of other treatments after this distillation is the same as Process 1.

TABLE 1.1

Conditions of Fatty Acid Distillation

| Factor | | Ex-1 | Ex-2 | Ex-3 | Ex-4 |
|---|---|---|---|---|---|
| Vacuum | (torr) | — | — | 1.5 | 2.0 |
| Temp. | (°C.) | — | — | 185 | 195 |
| Time | (hr) | — | — | 5.0 | 5.0 |

TABLE 1.2

Conditions of Methyl Esterification

| Step & Factor | Ex-1 | Ex-2 | Ex-3 | Ex-4 |
|---|---|---|---|---|
| Esterification | | | | |
| Catalyst | $H_2SO_4$ 0.2% | $H_2SO_4$ 0.15% | $H_2SO_4$ 0.05% | $H_2SO_4$ 0.02% |
| Temp (°C.) | 90 | 95 | 90 | 95 |
| Time (hr) | 3 | 4 | 1.5 | 1.5 |
| MeOH feed (l/hr) | 30 | 40 | 30 | 40 |
| Transesterification | | | | |
| Catalyst | $Ca(OH)_2$ 0.5% | NaOH 0.4% | NaOH 0.5% | KOH 0.5% |
| Temp. (°C.) | 50 | 55 | 55 | 55 |
| Time (hr) | 2.0 | 1.5 | 2.5 | 2.5 |
| Chelator | Ascorbic acid | Ascorbic acid | Ascorbic acid | Ascorbic acid |

TABLE 1.3

Conditions of Methyl Ester Distillation

| Factor | | Ex-1 | Ex-2 | Ex-3 | Ex-4 |
|---|---|---|---|---|---|
| Vacuum | (torr) | 1.5 | 2.0 | 1.0 | 1.0 |
| | (N/m²) | (200) | (267) | (133) | (133) |
| Temp. | (°C.) | 150 | 150 | 180 | 180 |
| Time | (hr) | 8 | 10 | 4.5 | 5.0 |

TABLE 1.4

Conditions of Crystallization and Filtration

| Step & Factor | Ex-1 | Ex-2 | Ex-3 | Ex-4 |
|---|---|---|---|---|
| Crystallization | | | | |
| Solvent (liters) | EtOH (20) | No addition | MeOH (20) | Hexane (20) |
| Cooling temp. (°C.) | 0 | 10 | 0 | 0 |
| Cooling time (hr) | 24 | 24 | 24 | 24 |
| Filtration | | | | |
| Filtration aid (%) | 3.0 | 2.0 | 4.0 | 4.0 |
| Filtration-pressure (kg/cm²) | 7 | 7 | 7 | 7 |

TABLE 1.5

Conditions of Ion-exchange Column

| Solvent | Ex-1 | Ex-2 | Ex-3 | Ex-4 |
|---|---|---|---|---|
| Purging (liters) | 95% EtOH 40 | 95% EtOH 30 | 95% EtOH 40 | 95% EtOH 30 |
| Detaching | 10% Boric acid | 10% Formic acid | 10% Lactic acid | 10% Malic acid |
| (liters) | 10 | 10 | 10 | 10 |
| Elution (liters) | 99% EtOH 60 | 99% EtOH 40 | 99% EtOH 50 | 99% EtOH 50 |

TABLE 1.6

Conditions of Evaporation

| Step & Factor | | Ex-1 | Ex-2 | Ex-3 | Ex-4 |
|---|---|---|---|---|---|
| 1st step | | | | | |
| Vacuum | (N/m²) | (2666) | (2666) | (2666) | (2666) |
| | (torr) | 20 | 20 | 20 | 20 |
| Temp. | (°C.) | 80 | 80 | 80 | 80 |
| Time | (hr) | 4 | 4 | 4 | 4 |
| 2nd step | | | | | |
| Vacuum | (N/m²) | (267) | (267) | (267) | (267) |
| | (torr) | 2 | 2 | 2 | 2 |
| Temp. | (°C.) | 100 | 100 | 100 | 100 |
| Time | (hr) | 1.5 | 2.0 | 1.5 | 1.5 |

TABLE 1.7

| | Condition of Washing and Drying | | | |
|---|---|---|---|---|
| Step & Factor | Ex-1 | Ex-2 | Ex-3 | Ex-4 |
| 1st washing | | | | |
| Water (liters, °C.) | 40, 60 | 40, 60 | 40, 70 | 40, 70 |
| Stirring (min.) | 20 | 20 | 20 | 20 |
| 2nd washing | | | | |
| Water (liters, °C.) | 20, 60 | 20, 60 | 20, 70 | 20, 70 |
| Stirring (min.) | 20 | 20 | 20 | 20 |
| Drying | | | | |
| Vacuum (N/m$^2$) | (400) | (533) | (400) | (533) |
| (torr) | 3 | 4 | 3 | 4 |
| Temp. (°C.) | 95 | 95 | 90 | 100 |
| Time (hr) | 1.5 | 1.5 | 1.5 | 1.5 |

TABLE 1.8

| | Conditions of Molecular Distillation | | | |
|---|---|---|---|---|
| Step & Factor | Ex-1 | Ex-2 | Ex-3 | Ex-4 |
| 1st step | | | | |
| Temp. (°C.) | 120 | 130 | 135 | 130 |
| Vacuum (torr) | 0.04 | 0.02 | 0.03 | 0.03 |
| (N/m$^2$) | (5.33) | (2.67) | (4.0) | (4.0) |
| 2nd step | | | | |
| Temp. (°C.) | 140 | 170 | 220 | 200 |
| Vacuum (torr) | 0.003 | 0.002 | 0.003 | 0.00 |
| (N/m$^2$) | (0.4) | (0.27) | (0.4) | |

TABLE 1.9

| | Conditions of Deodorization | | | |
|---|---|---|---|---|
| Factor | Ex-1 | Ex-2 | Ex-3 | Ex-4 |
| Temp. (°C.) | 160 | 180 | 200 | 200 |
| Vacuum (N/m$^2$) | (267) | (267) | (267) | (267) |
| (torr) | 2 | 2 | 2 | 2 |
| Steam feed (g/hr) | 500 | 400 | 300 | 450 |
| Time (hr) | 1.5 | 1.5 | 1.5 | 1.5 |

TABLE 2

The Concentration and Accumulated Yield of T and T3 on Each Step

| | Ex-1 | | Ex-2 | | Ex-3 | | Ex-4 | |
|---|---|---|---|---|---|---|---|---|
| Step | Conc. (%) | Yield (%) | Conc. (%) | Yield (%) | Conc. (%) | Yield (%) | Conc. (%) | Yield (%) |
| MATERIAL | 0.5 | 100 | 0.4 | 100 | 0.4 | 100 | 0.4 | 100 |
| FATTY ACID DISTILLATION | — | — | — | — | 2.1 | 97 | 2.4 | 98 |
| METHYL ESTERIFICATION | 0.5 | 98 | 0.4 | 99 | 2.1 | 95 | 2.4 | 94 |
| METHYL ESTER DISTILLATION | 8.2 | 95 | 10.1 | 96 | 8.4 | 91 | 9.5 | 90 |
| CRYSTALLIZATION AND FILTRATION | 8.3 | 90 | 10.1 | 92 | 8.4 | 88 | 9.5 | 88 |
| ION-EXCHANGE AND EVAPORATION | 83.2 | 85 | 87.6 | 80 | 85.1 | 78 | 93.4 | 78 |
| WASHING AND DRYING | 83.8 | 82 | 87.8 | 78 | 85.4 | 76 | 83.7 | 77 |
| MOLECULAR DISTILLATION | 96.2 | 75 | 97.9 | 71 | 95.2 | 70 | 96.6 | 70 |
| DEODORIZATION | (No significant changes in concentration or yield) | | | | | | | |

Those skilled in the art will appreciate that the invention described herein is susceptible to variations and modifications other than those specifically described. It is to be understood that the invention includes all such variations and modifications which fall within its spirit and scope.

What is claimed is:

1. A process for production of tocopherols and tocotrienols from palm fatty acid distillates, which comprises:

(a) treating the palm fatty acid distillates with an alkyl alcohol and catalysts to convert free fatty acids and glycerides into alkyl esters by esterification and transesterification, respectively;

(b) distilling the product of step (a) under reduced pressure to remove alkyl esters and leave the tocopherols and tocotrienols in the residue;

(c) cooling the residue of step (b) to crystallize substances with melting temperatures higher than tocopherols and tocotrienols and filtering off the crystalline material to leave the tocopherols and tocotrienols in the filtrate;

(d) treating the filtrate from step (c) by an ion-exchange procedure with an anionic exchange resin to produce a concentrated tocopherol and tocotrienol fraction in a solvent;

(e) removing the solvent from the tocopherol and tocotrienol fraction from step (d) by evaporation;

(f) washing and drying the product of step (e);

(g) subjecting the washed and dried product of step (f) to molecular distillation to produce a further concentrated tocopherol and tocotrienol product which as a content of at least 95 percent tocopherols and tocotrienols, and a cumulative yield of at least 70 percent; and (h) deodorizing the tocopherol and tocotrienol product of step (g).

2. The process as claimed in claim 1, further comprising, before the step (a) esterification, the step of pretreating the palm fatty acid distillates by distillation to remove free fatty acids therefrom.

3. The process as claimed in claim 2, wherein the pretreatment distillation step is carried out using a high heat-transfer rate falling film distillation column at temperature between 150° and 250° C., and a vacuum below 10 torr (1333 N/m$^2$).

4. The process as claimed in claim 1, wherein step (a) comprises using a catalyst selected from the group consisting of p-toluenesulfonic acid, hydrochloric acid and sulphuric acid for conversion of free fatty acids in the palm fatty acid distillates into alkyl esters, at a temperature between 65° and 110° C., and a reaction time of less than 3 hours.

5. The process as claimed in claim 1, wherein step (a) comprises using a catalyst selected from the group consisting of potassium hydroxide, sodium hydroxide and sodium methoxide for conversion of glycerides into alkyl esters at a temperature between 30° and 70° C., with a reaction time of at least 10 minutes.

6. The process as claimed in claim 1, further comprising treating the reaction mixture of step (a) with a chelating agent selected from the group consisting of ascorbic acid, phosphoric acid, maleic acid, citric acid and tartaric acid, before the step (b) distillation.

7. The process as claimed in claim 1, wherein the step (b) distillation comprises using a high heat-transfer rate falling film vacuum distillation column, operating at below 10 torr (1333 N/m$^2$) and at a temperature between 100° and 200° C.

8. The process as claimed in claim 1, wherein the step (d) treatment comprises using an eluting solvent selected from the group consisting of methanol, ethanol and hexane and using an acidic solution for desorbing tocopherols and tocotrienols from the anionic exchange resin.

9. The process as claimed in claim 1, wherein the step (e) solvent evaporation comprises using a falling film evaporator and a rotary short path evaporator in series, operating at temperatures of 50° C. and 130° C. respectively, and under reduced pressure.

10. The process as claimed in claim 1, wherein the step (g) molecular distillation is carried out at a temperature between 140° and 220° C., and under a vacuum below 0.05 torr (6.7 N/m$^2$).

11. The process as claimed in claim 1, wherein the starting material in step (a) has an initial concentration of less that 1 percent total tocopherols and tocotrienols.

12. A process for production of tocopherols and tocotrienols from palm fatty acid distillates, which comprises:

(a) distilling the palm fatty acid distillates to remove free fatty acids therein, using a high heat-transfer rate falling film distillation column at temperature between 150° and 250° C., and a vacuum below 10 torr (1333 N/m$^2$);

(b) treating the distillate of step (a) with an alkyl alcohol and a catalyst selected from the group consisting of p-toluenesulfonic acid, hydrochloric acid and sulphuric acid to convert free fatty acids into alkyl esters by esterification at a temperature between 65° and 110° C., and a reaction time of less than 3 hours;

(c) treating the reaction mixture of step (b) with a catalyst selected from the group consisting of potassium hydroxide, sodium hydroxide and sodium methoxide to convert glycerides into alkyl esters by transesterification, at a temperature between 30° and 70° C., and a reaction time of 10 minutes or more;

(d) treating the reaction mixture of step (c) with a chelating agent selected from the group consisting of ascorbic acid, phosphoric acid, maleic acid, citric acid and tartaric acid;

(e) distilling the product of step (d) with a high heat-transfer rate falling film vacuum distillation column, operating at less than 10 torr (1333 N/m$^2$) and at a temperature between 100° and 200° C. to remove a major part of the alkyl esters and leave the tocopherols and tocotrienols in the residue;

(f) cooling the residue of step (e) to crystallize substances with melting temperatures higher than tocopherols and tocotrienols and filtering off the crystalline material to leave the tocopherols and tocotrienols in the filtrate;

(g) treating the filtrate from step (f) by an ion-exchange procedure with an anionic exchange resin, using an eluting solvent selected from the group consisting of methanol, ethanol and hexane and using an acidic solution for desorbing tocopherols and tocotrienols from the resin;

(h) removing the solvent from the tocopherol and tocotrienol fraction from step (g) by evaporation using a falling film evaporator and a rotary short path evaporator in series, operating at temperatures of 50° and 130° C. respectively, and under reduced pressure;

(i) washing and drying the product of step (h);

(j) subjecting the product from step (i) to molecular distillation carried out at a temperature between 140° and 220° C., and under a vacuum below 0.05 torr (6.7 N/m$^2$), to produce a further concentrated tocopherol and tocotrienol product which has a content of at least 95 tocopherols and tocotrienols, ad a cumulative yield of at least 70 percent; and (k) deodorizing the tocopherol and tocotrienol product of step (j).

13. The process as claimed in claim 12, wherein the starting material in step (a) has an initial concentration of less than 1 percent total tocopherols and tocotrienols.

14. The process as claimed in claim 1 or 12, further comprising minimizing contact of tocopherols and tocotrienols with oxygen, by using nitrogen and/or nitrogen sparging throughout the various unit processes.

* * * * *

UNITED STATES PATENT AND TRADEMARK OFFICE
CERTIFICATE OF CORRECTION

PATENT NO. : 5,190,618
DATED : March 2, 1993
INVENTOR(S) : Abdul G. Md. Top et al.

It is certified that error appears in the above-identified patent and that said Letters Patent is hereby corrected as shown below:

Column 3, line 5, delete "such a" and substitute therefor --such as--.

Column 4, line 29, delete "N/m " and substitute therefor --$N/m^2$--.

<u>IN THE CLAIMS</u>

Col. 8, line 21, delete "as" and substitute therefor --has--.

Col. 10, line 37, delete "ad" and substitute therefor --and--.

Signed and Sealed this

Sixth Day of September, 1994

*Attest:*

BRUCE LEHMAN

*Attesting Officer*   *Commissioner of Patents and Trademarks*